United States Patent
Bogert et al.

(10) Patent No.: US 11,291,772 B2
(45) Date of Patent: Apr. 5, 2022

(54) SYRINGE AND PLUNGER ROD WITH STOPPER GUIDE

(71) Applicant: Becton, Dickinson and Company, Franklin Lakes, NJ (US)

(72) Inventors: Gerald Bogert, Maywood, NJ (US); Jason Richard Mondro, Sparta, NJ (US); Alfred Wesley Prais, Hewitt, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 294 days.

(21) Appl. No.: 16/484,213

(22) PCT Filed: Feb. 15, 2018

(86) PCT No.: PCT/US2018/018269
§ 371 (c)(1),
(2) Date: Aug. 7, 2019

(87) PCT Pub. No.: WO2018/152269
PCT Pub. Date: Aug. 23, 2018

(65) Prior Publication Data
US 2020/0023135 A1 Jan. 23, 2020

Related U.S. Application Data

(60) Provisional application No. 62/460,586, filed on Feb. 17, 2017.

(51) Int. Cl.
*A61M 5/315* (2006.01)
(52) U.S. Cl.
CPC .... *A61M 5/31513* (2013.01); *A61M 5/31515* (2013.01)

(58) Field of Classification Search
CPC .......... A61M 5/31513; A61M 5/31515; A61M 5/31501; A61M 2005/3106; A61M 2005/31521
See application file for complete search history.

(56) References Cited

U.S. PATENT DOCUMENTS

| 6,206,859 B1 | 3/2001 | Niedospial, Jr. | |
| 2004/0015120 A1* | 1/2004 | Berman | A61M 31/00 604/11 |

(Continued)

FOREIGN PATENT DOCUMENTS

| CN | 102834135 A | 12/2012 |
| CN | 102971031 A | 3/2013 |

(Continued)

OTHER PUBLICATIONS

Extended European Search Report dated Mar. 23, 2021, which issued in the corresponding European Patent Application No. 18754262.6.

(Continued)

*Primary Examiner* — Deanna K Hall
(74) *Attorney, Agent, or Firm* — Dickinson Wright PLLC

(57) ABSTRACT

A syringe assembly (10) has a syringe barrel (12), a plunger rod (14) and stopper (16) where the syringe barrel has an open end receiving the plunger rod and stopper in a sliding direction. The plunger rod includes a shaft (52) having a longitudinal axis with a first end having a coupling member (62) for coupling with the stopper. The shaft has a least one plunger rod support (82) extending radially outer from the shaft and spaced from the first end for cooperating with an inner surface of the syringe barrel (12) to resist lateral movement and tilting of the plunger rod relative to the longitudinal axis of the axial passage of the syringe barrel. The shaft in one embodiment has at least two spaced apart points of support (41) and (82) for maintaining the axis of (Continued)

the plunger rod on axis with the syringe barrel to limit twisting and tilting of the stopper thereby resisting distortion of the stopper that can cause leakage.

17 Claims, 4 Drawing Sheets

(56) References Cited

U.S. PATENT DOCUMENTS

| | | |
|---|---|---|
| 2006/0052748 A1 | 3/2006 | Coelho et al. |
| 2011/0034882 A1 | 2/2011 | Quinn et al. |
| 2011/0092903 A1 | 4/2011 | Caizza et al. |
| 2013/0110044 A1 | 5/2013 | Caizza et al. |
| 2014/0155826 A1 | 6/2014 | Yevmenenko |
| 2015/0105734 A1* | 4/2015 | Bryant .................. A61P 43/00 604/218 |

FOREIGN PATENT DOCUMENTS

| | | |
|---|---|---|
| EP | 2 298 392 A1 | 3/2011 |
| EP | 2 684 576 A2 | 1/2014 |
| JP | 2002-272843 A | 9/2002 |
| JP | 2010-246842 A | 11/2010 |
| JP | 2013-540490 A | 11/2013 |
| KR | 10-2005-0034849 A | 4/2005 |
| WO | 2008/136775 A2 | 11/2008 |
| WO | 2012/040051 A1 | 3/2012 |

OTHER PUBLICATIONS

Chinese Office Action dated Mar. 3, 2021, which issued in the corresponding Chinese Patent Application No. 201880012285.7, including Eng. translation.

International Search Report dated May 4, 2018, which issued in the corresponding PCT Patent Application No. PCT/US2018/018269.

* cited by examiner

SYRINGE AND PLUNGER ROD WITH STOPPER GUIDE

This application claims priority to U.S. Provisional Application No. 62/460,586 filed Feb. 17, 2017, which is hereby incorporated by reference in its entirety.

FIELD OF THE INVENTION

The present invention relates generally to a syringe and a plunger rod. The invention is particularly directed to a plunger rod provided with a stopper guide for assisting in maintaining a seal and preventing leakage when the plunge rod is off axis from the syringe barrel.

BACKGROUND OF THE INVENTION

Syringes are used for delivering a substance and for withdrawing and collecting arterial blood samples from the body of a patient. Various types of syringes have been devised that include a plastic or glass syringe barrel, a sealing elastomeric stopper, and a plunger rod. The syringes can include a self-sealing filter that allows passage of air out of the syringe during collection of a sample, while still preventing the passage of fluid being collected. This type of syringe having a filter allows for a sample to be collected without the need to aspirate the syringe, as is required with a syringe having a plunger rod and a plunger stopper.

A standard syringe having a plunger rod with the stopper attached can be subjected to side load applied to the plunger rod. A side load or force applied at an inclined angle with respect to the direction of travel of the plunder rod can result in distortion of the stopper relative the syringe barrel that may result in leakage around the stopper.

Typical syringes include a two-piece plunger rod assembly comprised of an elastomeric sealing stopper attached to a plunger rod. U.S. Pat. No. 5,314,416 to Lewis et al. discloses a low friction syringe assembly having a typical two-piece plunger rod and a plunger tip assembly. The sealing stopper and plunger rod are assembled together in a separate operation prior to assembly with a syringe barrel. A silicone lubricant is usually used on the interior wall of the syringe barrel to facilitate sliding movement of the elastomeric sealing stopper against the interior wall of the syringe barrel. A needle can be connected to the syringe to dispense the contents. The needle can also access a blood vessel for collecting a blood sample where the syringe is thereafter aspirated by the holding the syringe in a fixed position and drawing the plunger rearward within the syringe barrel to draw a blood sample into the syringe barrel.

After completion of the sample collection, the needle is removed and the syringe containing the collected sample is then transported to the laboratory. The plunger that is protruding from the syringe barrel can make handling and transportation of the syringe difficult and special care has to be taken not to dislodge the plunger that can cause leakage. When the plunger rod is withdrawn from the syringe barrel, the plunger rod may not be stable and can deflect to a position where the axis of the plunger rod is not aligned with the axis of the syringae barrel. The stopper can be deflected at an angle that can cause leakage.

While the prior devices have been generally suitable for the intended use, there is a continuing need in the industry for improved devices for collecting and delivering a substance to a patient.

SUMMARY OF THE INVENTION

One embodiment of the invention is directed to a syringe and a plunger rod for dispensing and delivering a substance to a patient or for collecting a sample from patient. The invention is particularly directed to a syringe and plunger rod that reduces the incidence of leakage between the stopper and the syringe barrel.

The syringe in one embodiment has a syringe barrel with an open end for receiving a plunger rod and an outlet end for dispensing or collecting a fluid. The plunger rod has a stopper coupled to one end of the plunger rod for sliding within the syringe barrel to dispense or collect the fluid. The plunger rod is configured to slide within the syringe barrel while maintaining a stable axial position within the syringe barrel.

One aspect of the present invention is to provide a plunger rod having an annular plate forming a rib spaced from the distal end of the rod and spaced from the stopper that cooperates with the inner surface of the syringe barrel to stabilize and maintain the axis of the plunger rod on the axis of the syringe barrel.

A further aspect of the invention is to provide a plunger rod for supporting a stopper that slides within a syringe barrel where the plunger rod has two or more axially spaced points of support that can complement or engage the inner surface of the syringe barrel. In one embodiment, two or more plates or ribs are spaced apart a distance to limit tilting of the plunger rod off axis relative to the axis of the syringe barrel thereby preventing distortion of the stopper. The two spaced apart points of support maintain the longitudinal axis of the plunger rod and the longitudinal axis of the stopper parallel to the longitudinal axis of the syringe barrel.

The foregoing and/or other aspects of the present invention are achieved by providing a plunger rod for a syringe where the plunger rod has a longitudinally extending shaft with a distal first end for coupling to a stopper, and a proximal second end opposite the distal end for operating the plunger rod. An annular plate forming a rib is positioned at the first end and oriented to engage the inner surface of a syringe barrel during sliding of the plunger rod within the syringe barrel to maintain the axis of the plunger rod parallel to the longitudinal axis of the syringe barrel. By maintaining the plunger rod on the axis of the syringe barrel, the plunger remains on the axis of the syringe barrel to reduce the occurrence of leakage.

The features of the present invention are achieved by providing a syringe assembly having a syringe barrel, a plunger rod and a stopper coupled to the distal end of the plunger rod. The plunger rod has a shaft with a distal end and a proximal end. A coupling member extends from the distal end for supporting the stopper. At least one support is positioned at: the distal end for cooperating with the syringe barrel to limit tilting of the plunger rod relative to the syringe barrel.

The various features of the present invention are also achieved by providing a plunger rod with at least two spaced apart supports providing at least two supporting points for the plunger rod and supporting the position of the plunger rod within the syringe barrel during use. The shaft includes a base plate at the distal end forming a first support point and for mating with and supporting the stopper. The second support point is provided by a support spaced axially from the based plate a distance to limit tilting of the plunger rod within the syringe barrel. In one embodiment, the support is a support plate or an outwardly extending projection.

The features of the invention are further attained by providing a syringe assembly including a syringe barrel and a plunger rod. The syringe barrel has an axial dimension with an axial passage with an open end. The plunger rod has a shaft with a first end with a stopper coupled to the first end for sliding in the syringe barrel. The shaft of the plunger rod has a second end for actuating the plunger rod by the user. At least one rib extends outward from the shaft to engage the inner surface of the syringe barrel when the plunger rod is tilted relative to the axis of the syringe barrel.

The features of the invention provide at least one support, such as a support plate, extending outward from the plunger shaft where the support plate is spaced from the first end a distance to stabilize and resist tilting of the plunger rod when the plunger rod is withdrawn toward the open end of the syringe barrel.

A syringe assembly in one embodiment includes a syringe barrel having an open end and an axial passage and a plunger rod. The plunger rod includes a shaft having a longitudinal axis with a first end and a second end opposite said first end. A stopper support is provided at the first end forming a first contact point with an inner surface of said syringe barrel. A coupling member is provided on the stopper support at the first end and a stopper is coupled to the coupling member. The stopper has an outer dimension for sliding in the axial passage of said syringe. The shaft has at least one plunger rod support extending radially outward from the shaft and spaced from the first end forming at least one second contact point with the inner surface of the syringe barrel. The at least one plunger rod support has an outer dimension for engaging the inner surface of the syringe barrel to resist lateral movement and tilting of the plunger rod relative to the syringe barrel. The plunger rod support is spaced from the stopper support a distance of about 1 to 1.5 times an inner diameter of the syringe barrel.

Additional and/or other aspects and advantages of the present invention will be set forth in part in the description that follows and, in part, will be apparent from the description, or by practicing of the invention.

BRIEF DESCRIPTION OF THE DRAWINGS

The above and/or other aspects and advantages of embodiments of the invention will be more readily appreciated from the following detailed description, taken in conjunction with the accompanying drawings, in which.

DETAILED DESCRIPTION OF EXEMPLARY EMBODIMENTS

Figure 1:
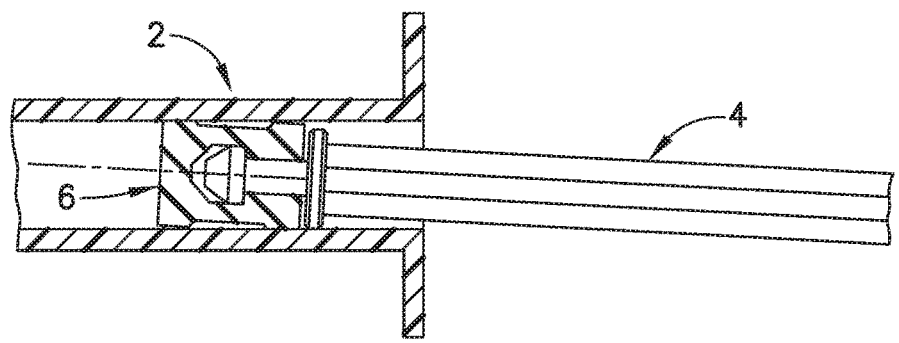
FIG. 1 is a side view in cross section of a standard syringe plunger rod assembly.

Reference is made in detail to embodiments of the present invention, examples of which are illustrated in the accompanying drawings, wherein like reference numerals refer to the like elements throughout. The descriptions of these embodiments exemplify the present invention by referring to the drawings.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are exemplary embodiments of the invention. Specific dimensions and other physical characteristics related to the embodiments disclosed herein are not to be considered as limiting. The embodiments are not intended to be mutually exclusive so that the features of one embodiment can be combined with other embodiments.

As used herein, the term "proximal" refers to a location assembly according to the embodiments of this invention that, during normal use, is closest to the clinician using the device and farthest from the patient in connection with whom the device is used. Conversely, the term "distal" refers to a location on the assembly of this invention that, during normal use, is farthest from the clinician using the device and closest to the patient in connection with whom the device is used. Furthermore, the term "proximal direction" indicates a direction of movement away from the patient and toward the user of the blood collection assembly, whereas the term "distal direction" indicates a direction of movement away from the user of the assembly and toward the patient.

FIG. 1 is side view in cross section of a standard syringe barrel 2 and a plunger rod 4 having a stopper at one end. The plunger rod of FIG. 1 has an outer dimension that is slightly less than the inner dimension of the syringe barrel to be able to slide axially within the syringe barrel. As a result, the lateral force applied to the plunger rod causes the plunger rod and the stopper to move to a position that are not parallel to the axis of the syringe barrel where the stopper can distort and cause leakage around the stopper. When the plunger rod is retracted to a position shown in FIG. 1 within the axial passage of syringe barrel 2, the plunger rod can tilt off axis relative to the axis of syringe barrel 2. This can result in ribs of the stopper compressing or distorting on one side as shown resulting in leakage around stopper 6. The ribs can also be lifted off contact with the inner surface of syringe barrel 2 when a side load is applied to plunger rod 4. The pressure within the syringe barrel can then result in leakage around the ribs of the stopper when the stopper is tilted off axis.

Referring to FIGS. 2-11, the syringe assembly 10 of the invention includes a syringe barrel 12, a plunger rod 14, and stopper 16 coupled to the plunger rod 14. The syringe barrel 12 can be a standard syringe barrel having a substantially cylindrical body 18 with a distal first end 20 defining an outlet end and a proximal second end 22 defining an open end for receiving the plunger rod and stopper. The outlet end in the embodiment shown has a conical shaped end portion 24 that converges to an outlet nozzle 26. The nozzle 26 can receive and support a cannula or can be coupled to a suitable delivery device for delivering the contents of the syringe to a patient. In other embodiments, nozzle 26 can be a luer fitting.

The open end 22 includes a flange 28 for manipulating syringe barrel 12 in a standard manner. The syringe barrel 12 is formed with a side wall 30 having an axial passage 32 defining an inner chamber for containing the substance to be delivered by sliding plunger rod 14 and stopper 16 toward first open end 20. The axial passage 24 is formed with a smooth inner surface 34. In the embodiment shown, barrel 12 has a substantially cylindrical shaped side wall 30. A suitable lubricant, such as a silicone lubricant, can be applied to the inner surface to assist in the sliding of the stopper within the syringe barrel. The syringe barrel can be made of glass or a suitable rigid clear plastic material. The plunger rod can also be made of a rigid plastic material.

The syringe assembly 10 of the invention is constructed to reduce the incidence of leakage between stopper 16 and the inner surface of the syringe barrel during use. The plunger rod 16 is configured to maintain the plunger rod on the intended axis and in line with the axis of the syringe barrel. The plunger rod 16 includes at least one and typically two points of support with respect to the syringe barrel to limit the tilting of the plunger rod with respect to the syringe barrel and limit distortion of the stopper.

Figure 2:
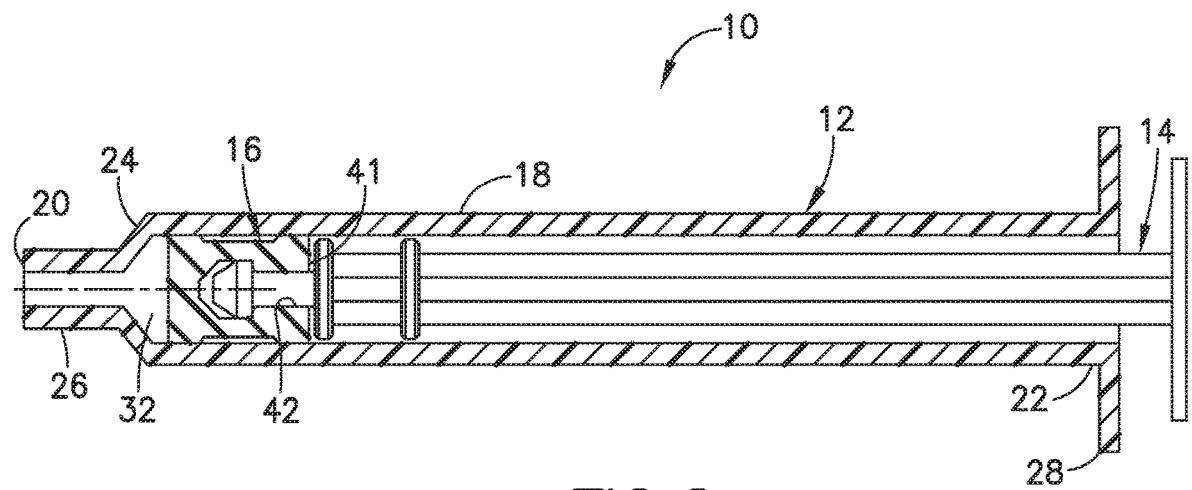
FIG. 2 is a cross sectional side view showing the syringe assembly of the invention where the plunger rod is received in the syringe barrel.
Figure 3:
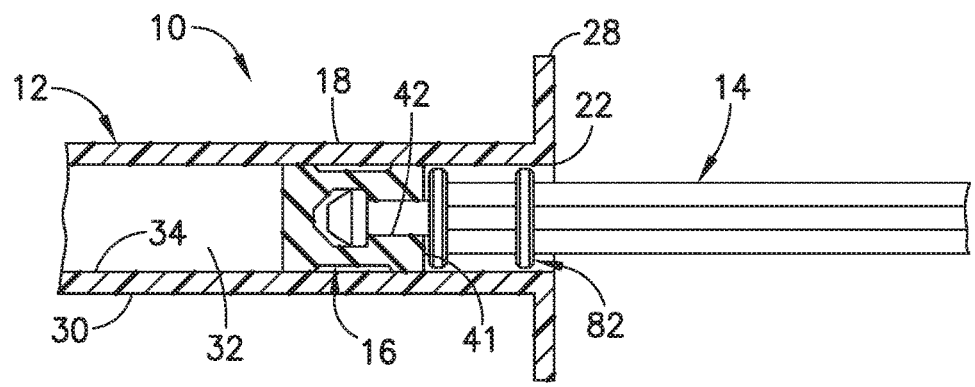
FIG. 3 is a cross-sectional view showing the plunger rod retracted to a position toward the open end of the syringe barrel.
Figure 4:
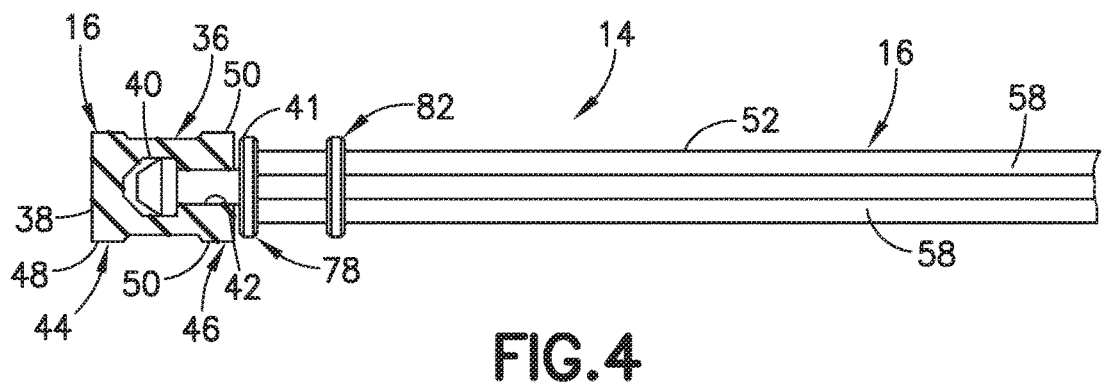
FIG. 4 is a partial cross-sectional view illustrating plunger rod and stopper.

As shown in FIGS. 2-4, stopper 16 is coupled to plunger rod 14 to slide within the axial passage 32 of the syringe barrel 12 and maintain contact with the inner surface 34 to provide a seal sufficient to dispense the contents of the syringe without leakage between the stopper and the syringe barrel. The shape of stopper 16 provides sufficient contact surface area to form a suitable seal while limiting the contact surface to enable the stopper to slide easily within the syringe barrel. A large surface area on the stopper in contact with the inner surface of the syringe barrel can provide a high friction and interference such that sliding of the stopper becomes difficult under normal use.

In the embodiment show, stopper 16 has a substantially cylindrical shape with an outer annular surface 36, an outer end 38, and a recess 40 at an inner end 41 opposite the outer end 38. The outer end 38 provides an end surface for contacting the contents of the syringe and dispensing the contents from the syringe barrel. Recess 40 is formed with an annular lip 42 that extends radially inward for coupling to plunger rod 14.

Outer surface 36 of stopper 16 in the embodiment shown in FIGS. 3 and 4 has a leading rib 44 and trailing rib 46 for contacting the inner surface 34 of syringe barrel 12. Ribs 44 and 46 have a substantially annular shape and extend radially outward from the body of stopper 16. Ribs 44 and 46 have outer annular faces 48 and 50, respectively, for contacting the inner surface 34 of syringe barrel 12 and forming a seal. The outer annular faces in the embodiment shown have a substantially cylindrical shape to provide a sufficient contact area with syringe barrel 12. The annular shaped ribs 44 and 46 are spaced apart a distance to provide stability to the stopper during movement and use and reduce the incidence of the stopper twisting or tilting and maintaining the axis of the stopper oriented parallel and coaxial to the axis of the syringe barrel. In one embodiment, a lubricant can be provided on the inner surface of the syringe barrel to assisting in sliding movement of the stopper with respect to the syringe barrel. The stopper can be made of a suitable elastomeric material, such as isoprene rubber, as known in the art.

Referring to FIGS. 5-11, plunger rod 14 has a longitudinal shaft 52 with a proximal end 54 and distal end 56. Shaft 52 is formed with outwardly extending ribs 58 to provide strength and resist bending and deflection during use while limiting the amount of material needed to form the shaft. In one embodiment, four radially extending ribs 58 are provided to form a shape for providing sufficient strength to the shaft. A proximal end 54 is provided with an operating flange 60 for the operator during use. Ribs 58 extend outwardly a distance to define an outer dimension of shaft 52 that is slightly less than an inner diameter of syringe barrel 12 so that the shaft can slide within the syringe barrel without interference or friction that would inhibit the sliding movement of the plunger rod 14 during use. In one embodiment, ribs 58 extend the length of shaft 52.

Figure 5:
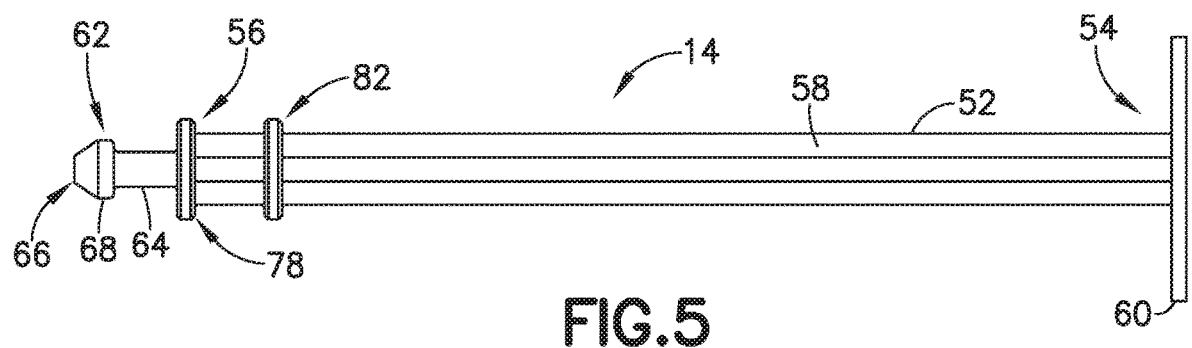
FIG. 5 is a front perspective side view illustrating the plunger rod.
Figure 6:
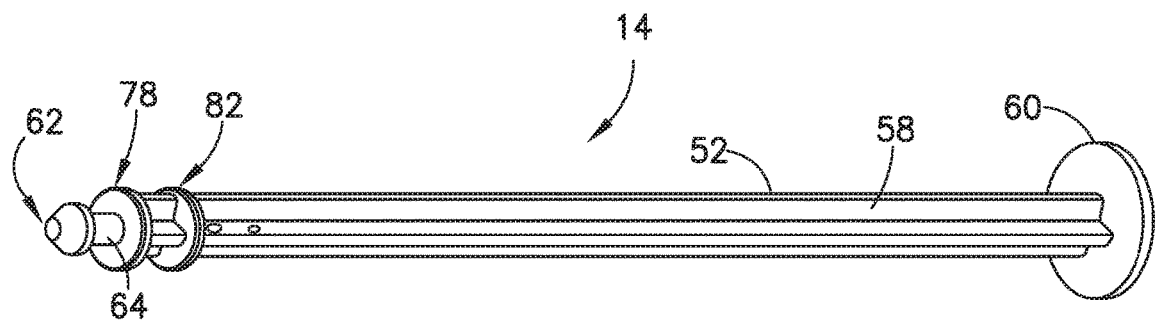
FIG. 6 is a front perspective view of the plunger rod.
Figure 7:
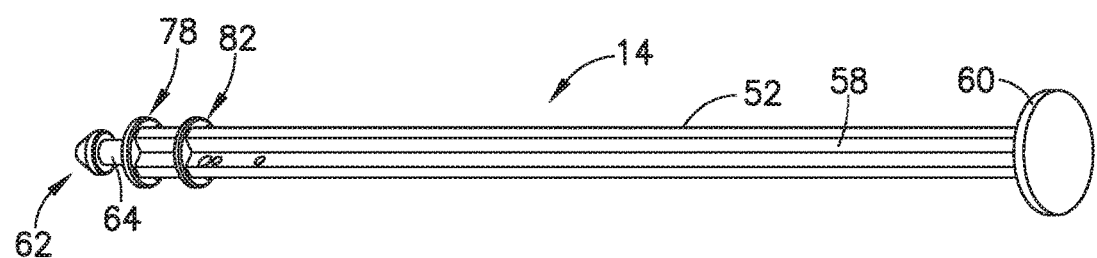
FIG. 7 is a rear perspective view of the plunger rod.
Figure 8:
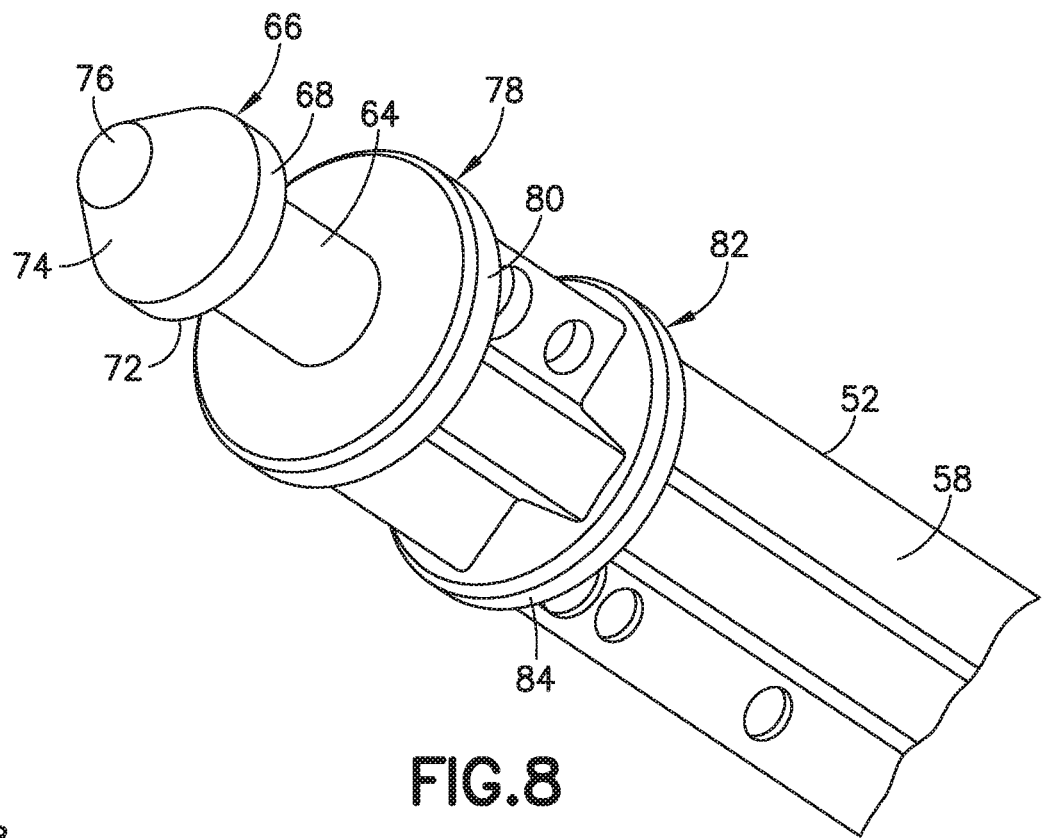
FIG. 8 is a front perspective view of a coupling end of the plunger rod.

Distal end 56 of shaft 52 includes a coupling member 62 for receiving and supporting stopper 16. The coupling member 62 includes a post 64 and an enlarged head 66 for mating with stopper 16. As shown in FIG. 5, post 64 has a diameter less than the outer dimension of shaft 52 and extends in an axial direction from the distal end 56. The head 66 protrudes from the axial end of post 64 and has a diameter larger than the diameter of post 64.

The head 66 has an outer annular face 68 and a bottom face 70 extending radially outward from post 64 to form a ledge 72 with outer annular face 68 for coupling with the stopper 16. The axial end of the head 66 has a conical shaped portion 74 converging to a substantially flat axial face 76 as shown in the end view of FIG. 11 and the side view of FIG. 10. As shown in FIG. 4, recess 40 of stopper 16 receives head 66 where annular lip 42 of stopper 16 engages ledge 72 and is retained on head 66.

Figure 9:
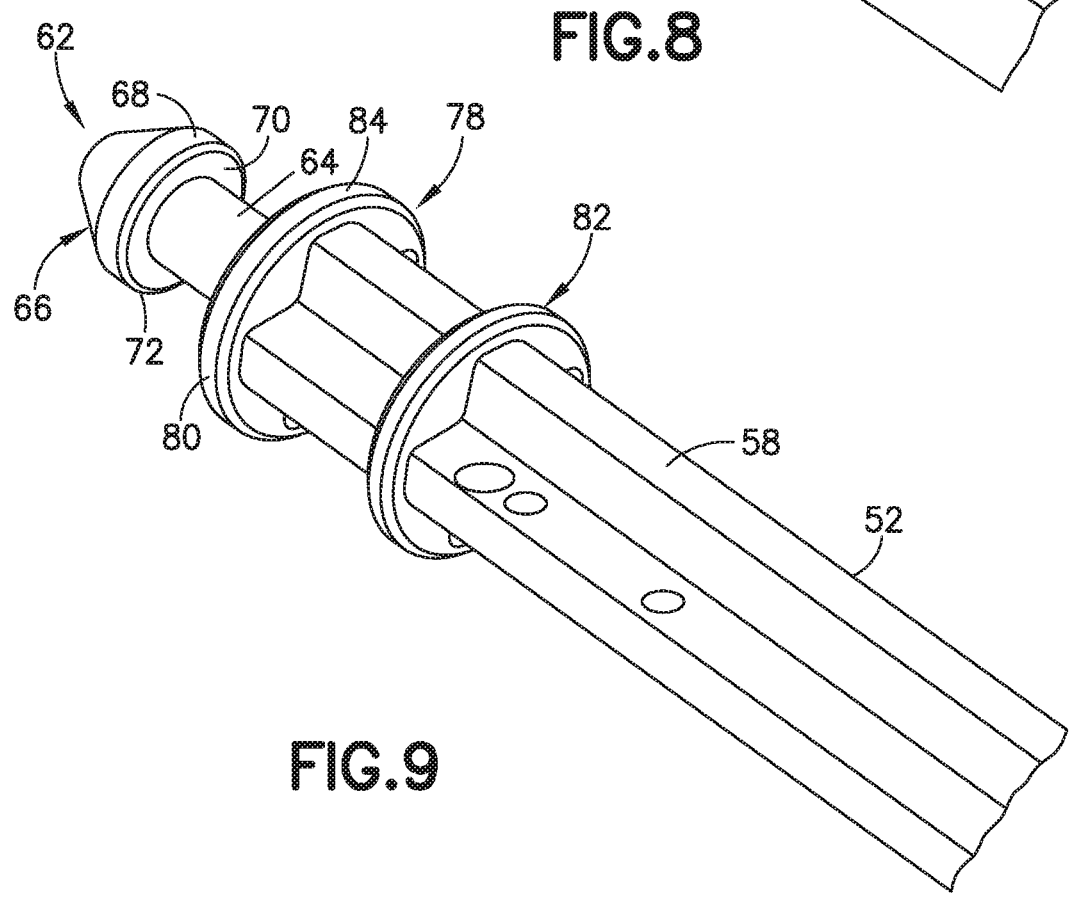
FIG. 9 is a rear perspective view of the coupling end of the plunger rod.
Figure 10:
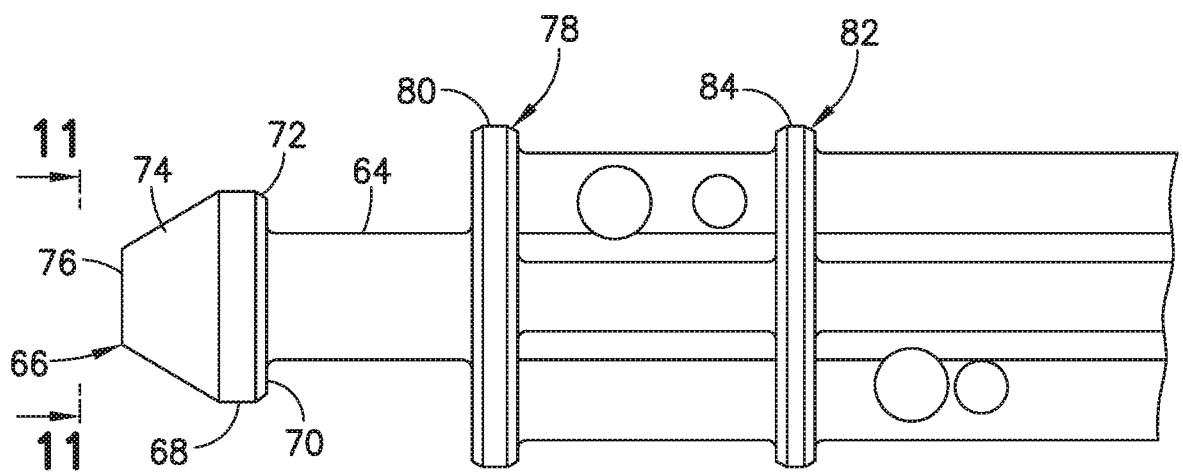
FIG. 10 is an enlarged side view of coupling end of the plunger rod.
Figure 11:
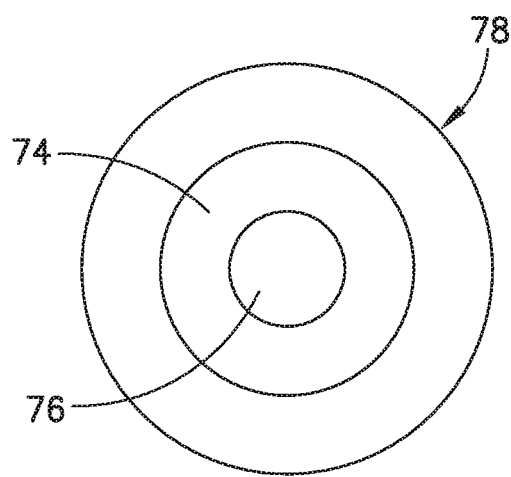
FIG. 11 is an end view of the plunger rod taken along line 11-11 of FIG. 10.

The shaft 52 includes a base plate 78 forming a push plate at distal end 56 at the base of post 64 so that post 64 extends axially from plate 78. Base plate 78 has a substantially circular shape with an outer annular edge 80 and an axial thickness to provide sufficient support for stopper 16 during the forward movement of plunger rod 14 in use. The outer annular edge 80 provides a first support point for plunger rod 14 and stopper 16 relative to syringe barrel 12. As shown in FIG. 4, base plate 78 has an outer dimension slightly less than an outer dimension of stopper 16 and a diameter slightly less than the inner diameter of syringe barrel 12 to enable sliding within syringe barrel 12 and supporting the plunger rod and stopper during use. The base plate 78 has an outer dimension to slide within axial passage 32 of syringe barrel 12 without interfering with the movement of plunger rod 14. As shown in FIG. 9, base plate 78 has an outer dimension greater than the outer dimension of ribs 58 of shaft 52.

A support 82 is formed on shaft 52 and spaced axially from base plate 78 a distance to stabilize the plunger rod when received in syringe barrel 12 and limit tilting of the shaft off axis from the axis of the syringe barrel when a side load is applied. In the embodiment shown, the support member 82 has a circular shape corresponding to the inner shape and dimension of the inner surface of the syringe barrel. The support can have other shapes that are able to contact the inner surface of the syringe barrel and support the plunger rod. In an alternative embodiment, the support can be a plurality of prongs or ribs spaced apart a distance to support the plunger rod. The support is spaced from the base plate a distance equal to or greater than the inner diameter of the syringe barrel.

In the embodiment shown, the support is a support plate 82 extending radially outward from the shaft 52 and has an outer radial outer dimension substantially the same as base plate 78. The outer annular edge 84 of support plate 82 is substantially coaxially aligned with the outer annular edge of base plate 78. Support plate 82 has an outer diameter slightly less than the inner diameter of syringe barrel 12 to allow sliding movement and maintain support of plunger rod 14 within the syringe barrel.

The outer diameter of the base plate and support plate has a nominal diameter less than the inner diameter of the syringe barrel for sliding and supporting the plunger rod on the axis of the syringe barrel when a side load is applied to the plunger rod. The axial spacing between the base plate and support plate is sufficient to contact the inner surface of the syringe barrel during normal use of the syringe. The spacing is selected so that the support plate is retained within the syringe barrel when the syringe is filed with contents prior to dispensing the contents to stabilize the plunger rod within the syringe barrel. The support plate is oriented relative to the base plate so that support plate is positioned within the syringe barrel throughout the normal operating position of the plunger rod with respect to the syringe barrel.

The spacing between the base plate and support plate can vary depending on the inner diameter of the syringe barrel and the axial length of the plunger rod and the axial length of the stopper. The spacing between the base plate and the support plate is a distance that prevents distortion of the stopper that can otherwise cause leakage. In one embodiment, the spacing between the base plate and the support plate can be equal to or greater than an inner diameter of the syringe barrel. Typically, the axial spacing between the base plate and the support plate is not less than an inner diameter of the syringe barrel. The spacing between the base plate and the support plate relative to the inner diameter of the syringe barrel in one embodiment can be about 1:1 to 2:1. In one embodiment, the ratio of the axial spacing between the base plate and support plate relative to the inner diameter of the syringe barrel is about 1:1 to about 1.5:1. In another embodiment, the axial spacing between the base plate and the support plate is about 1:1 with respect to the inner diameter of the syringe barrel so that the axial spacing is about equal to the inner diameter of the syringe barrel. In a further embodiment, the spacing between the base plate and the support plate is about 1 to 1.5 times the inner diameter of the syringe barrel.

As shown in FIGS. 2 and 3, plunger rod 14 has a length complementing the axial length of the chamber of syringe barrel 12 for dispensing the contents of the syringe assembly 10. FIG. 2 shows plunger rod 14 in the forward position relative to the syringe barrel 12 either before filling the syringe or after dispensing the contents of syringe 12. As shown in FIG. 2, ribs 44 and 46 of stopper 16 contact with inner surface 34 of syringe barrel 12 to form a fluid tight seal dispensing the contents of the syringe and preventing leakage through open end 22.

FIG. 3 shows plunger rod 14 and stopper 16 in a retracted position relative to the syringe barrel. As shown, base plate 78 and support plate 82 stabilize plunger rod 14 and prevent deflection or tilting of plunger rod 14 with respect to syringe barrel 12 thereby maintaining stopper 16 in a position axially aligned with the axis of syringe barrel 12 to prevent leakage that can occur when the stopper is tilted off axis. During use, the forward force applied to the plunger rod by the user can result in a force being directed at an inclined angle with respect to axis of the syringe barrel that cause the stopper to twist or tilt off axis. The plates 78 and 82 are provided with minimal clearance between the inner surface of the syringe barrel to resist tilting of the plunger rod and resist deflection or distortion of the stopper during use.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of the appended claims and equivalents thereof.

The invention claimed is:

1. A plunger rod configured for use with a syringe barrel, said plunger rod comprising:
a shaft having a longitudinal axis with a first end and a second end opposite said first end;
a coupling member at said first end configured for coupling to a stopper, said shaft having a base plate contacting and supporting a proximal end of said stopper with respect to said syringe barrel;
said shaft having at least one support plate with an outer diameter substantially the same as an outer diameter of said base plate and extending radially outward from said shaft and having a dimension for engaging an inner surface of the syringe barrel, said support plate spaced from said base plate a distance to resist lateral movement of said plunger rod relative to the syringe barrel and resist leakage around said stopper when said syringe barrel is filled with a substance and said plunger rod is in a proximal position with respect to said syringe barrel prior to dispensing the substance from the syringe barrel.

2. The plunger rod according to claim 1, wherein the coupling member comprises a post extending axially from said shaft and an enlarged head for coupling with the stopper.

3. The plunger rod according to claim 2, wherein said base plate has an annular shape extending radially outward from said shaft and configured to support an end of the stopper.

4. The plunger rod according to claim 3, wherein said support plate has an annular shape and is spaced axially from said annular base plate toward said second end.

5. The plunger rod according to claim 4, wherein the annular support plate has a radial dimension complementing a radial dimension of said base plate to stabilize the plunger rod when received in a syringe barrel and when said plunger rod is in the proximal position.

6. The plunger rod according to claim 4, wherein said syringe barrel has an internal diameter, and where said support plate is spaced from said base plate a distance of about 1 to 1.5 times the inner diameter of the syringe barrel.

7. A syringe assembly comprising:
a syringe barrel having an open end and an axial passage;
plunger rod including a shaft having a longitudinal axis with a first end and a second end opposite said first end;
a coupling member at said first end and a stopper coupled to said coupling member, said stopper having an outer dimension for sliding in said axial passage of said syringe;
said shaft having a base plate at said first end contacting and supporting said stopper and at least one support plate extending radially outward from said shaft and spaced proximally from said base plate at said first end a distance of about 1:1 to about 2:1 relative to an inner diameter of said syringe, said base plate and at least one support plate having an outer dimension for engaging an inner surface of the syringe barrel to resist lateral movement and tilting of said plunger rod relative to the syringe barrel and leakage around the stopper when said syringe barrel is filled with a substance and said plunger is in a proximal position with respect to said syringe barrel before dispensing the substance from said syringe barrel.

8. The syringe assembly according to claim 7, wherein said base plate has an annular shape extending radially outward from said shaft and configured for supporting said stopper.

9. The syringe assembly according to claim 7, wherein the support plate has a radial dimension complementing a radial dimension of said base plate to stabilize the plunger rod when received in the syringe barrel.

10. The syringe assembly according to claim 8, wherein said annular support plate has an outer dimension substantially the same as an outer dimension of said base plate.

11. The syringe assembly according to claim 7, wherein the stopper has a first annular rib at a distal end and a second annular rib as a proximal end of said stopper.

12. The syringe assembly according to claim 7, wherein said support plate is spaced axially from said base plate a distance equal to or greater than an inner diameter of the syringe barrel.

13. The plunger rod of claim 7, wherein the axial spacing between the base plate and the support plate is 1:1 to 1.5:1 relative to the inner diameter of the syringe barrel.

14. A syringe assembly comprising:
a syringe barrel having an open end and an axial passage;
a plunger rod including a shaft having a longitudinal axis with a first end and a second end opposite said first end, and a stopper support at said first end forming a first contact point with an inner surface of said syringe barrel;
a coupling member on said stopper support at said first end and a stopper coupled to said coupling member, said stopper having an outer dimension for sliding in said axial passage of said syringe;
said shaft having at least one plunger rod support plate extending radially outward from said shaft and spaced from said first end forming at least one second contact point with the inner surface of the syringe barrel, said at least one plunger rod plate support having an outer dimension for engaging the inner surface of the syringe barrel to resist lateral movement and tilting of said plunger rod relative to the syringe barrel and to inhibit leakage around said stopper when said plunger rod is in a proximal position and said syringe barrel is filled with a substance, and where said plunger rod support plate is spaced from said stopper support a distance of about 1 to 1.5 times an inner diameter of said syringe barrel.

15. The syringe assembly of claim 14, wherein said stopper support is a circular support plate extending radially outward from said plunger rod.

16. The syringe assembly of claim 15, wherein said plunger rod support plate is a circular plate extending outwardly from said plunger rod.

17. The syringe assembly of claim 16, wherein said plunger rod support plate has diameter substantially equal to a diameter of said stopper support plate.

* * * * *